United States Patent
Jakobsson (10) Patent No.: US 9,471,772 B2
(45) Date of Patent: Oct. 18, 2016

(54) PASSWORD CHECK BY DECOMPOSING PASSWORD

(75) Inventor: Bjorn Markus Jakobsson, Maountain View, CA (US)

(73) Assignee: PAYPAL, INC., San Jose, CA (US)

( * ) Notice: Subject to any disclaimer, the term of this patent is extended or adjusted under 35 U.S.C. 154(b) by 0 days.

(21) Appl. No.: 13/460,378

(22) Filed: Apr. 30, 2012

(65) Prior Publication Data

US 2012/0284783 A1 Nov. 8, 2012

Related U.S. Application Data

(60) Provisional application No. 61/492,294, filed on Jun. 1, 2011.

(51) Int. Cl.
*G06F 7/04* (2006.01)
*G06F 21/46* (2013.01)

(52) U.S. Cl.
CPC .................................. *G06F 21/46* (2013.01)

(58) Field of Classification Search
CPC ...................................................... G06F 21/31
USPC ...................................................... 726/1–3, 6
See application file for complete search history.

(56) References Cited

U.S. PATENT DOCUMENTS

| | | | |
|---|---|---|---|
| 8,561,174 B2 * | 10/2013 | Fischer | 726/21 |
| 2008/0244690 A1 * | 10/2008 | Kulkarni et al. | 726/1 |
| 2009/0276257 A1 * | 11/2009 | Draper et al. | 705/7 |
| 2009/0313696 A1 * | 12/2009 | Himberger et al. | 726/22 |

\* cited by examiner

*Primary Examiner* — Anthony Brown
(74) *Attorney, Agent, or Firm* — Haynes and Boone, LLP (57) ABSTRACT

A proposed password is decomposed into basic components to determine and score transitions between the basic components and create a password score that measures the strength of the proposed password based on rules, such as concatenation, insertion, and replacement. The proposed password is scored against all known words, such as when a user is first asked to create a password for an account or access. The proposed password can also be scored against one or more previous passwords for the user, such as when the user is asked to change the user's previous password, to determine similarity between the two passwords.

27 Claims, 5 Drawing Sheets

PASSWORD CHECK BY DECOMPOSING PASSWORD

CROSS REFERENCE TO RELATED APPLICATION

This application claims priority to U.S. Provisional Patent Application Ser. No. 61/492,294, filed Jun. 1, 2011.

BACKGROUND

1. Field of the Invention

The present invention generally relates to passwords, and in particular, to checking a password strength.

2. Related Art

Passwords are used to provide security to a user's sensitive information and to grant a user access to content. For example, a user may be required to enter a correct password to access certain information, such as financial information, and perform certain transactions, such as making a payment. Thus, secure passwords are important to prevent unauthorized use or access to a user's account or information. Typically, the more obscure the password or unrelated it is to the user, the harder it is for someone to correctly guess or determine the actual user password. In addition, systems or sites may require the user to periodically change the password for additional security. Thus, it is important for the user to select or change to a password that is strong, as opposed to weak, and not easily determined by others even with knowledge of the previous password.

However, users typically select or change passwords that are easy to remember. For the former, users may select a word, a phrase, a number, or a combination thereof that makes sense for the user, such as a name, a birthday, an address, or the like. For the latter, the user may slightly modify the previous password by adding a number or replacing a number with the next number. These passwords may be easy for fraudsters to obtain, such as by guessing or other more analytical methods. This may then allow an unauthorized user to access a user account, including make unauthorized payments or withdrawals, engage in identity theft, etc.

Thus, there is a need to ensure a proposed user password is strong.

SUMMARY

According to one embodiment, a proposed password is decomposed into basic components to determine and score transitions between the basic components and create a password score that measures the strength of the proposed password.

In one embodiment, a proposed password is scored against all known words, such as when a user is first asked to create a password for an account or access.

In another embodiment, a proposed password is scored against one or more previous passwords for the user, such as when the user is asked to change the user's previous password.

In one embodiment, a password is analyzed to determine all words or numbers (referred to generally to as words) contained within the password. A word may be appended to the beginning or end of another word or inserted within another word. Once the words have been identified, a series of rules are applied. In one embodiment, a first rule is concatenation, in which a word is appended to the beginning or end of another word. A score is then determined. Next, a second rule is applied, which is insertion, and the score updated. Insertion is when a word is placed within another word. A third rule, replacement, is then applied. Replacement is when one or more characters are replaced in the word. The password score is again updated based on the replacement analysis. Each rule can have a different weight. Also, each rule can have different weights within a rule. The final score of the password can then be used to determine its strength or weakness. If the score indicates a very weak password, the user may be asked to submit a different password.

In another embodiment, one or more previous passwords may be compared with a newly proposed password to determine how similar they are. In one embodiment, only the most recent password is compared. The comparison can be based on the rules above. If the proposed password is too similar to the previous password(s), the user may be asked to submit a new replacement password. This may be the case even when the password appears very strong by itself, however, it was only changed by the next sequential number from the previous password.

As a result, new and replacement passwords can be checked for strength to increase the security of a user proposed password.

These and other features and advantages of the present invention will be more readily apparent from the detailed description of the embodiments set forth below taken in conjunction with the accompanying drawings.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

A user typically submits a proposed password at the request of a site, system, or merchant as part of an account creation or maintenance process. Examples of sites or systems requiring a user to submit a proposed password include financial institutions, merchants, educational institutions, law firms, and the like, generally referred to herein as service providers. For example, a payment provider, such as PayPal, Inc. of San Jose, Calif., may request the user to enter a proposed password (along with a user identifier) in order to create an account with PayPal. After a year or another time period, PayPal may request the user to submit a new password for security reasons. The user may be requested to submit a new password at other non-periodic times, such as when the user account has been compromised or suspected of being compromised.

Once a password is requested, such as through a user device, the user may enter and communicate the proposed password from the user device to the site. User devices may include a smart phone, a computing tablet, a PC, or other computing devices. The proposed password may be communicated electronically, such as through a mobile, wireless, or cable network, to a server, processor, or other computing device. The computing device of the site then determines whether the proposed password is acceptable.

Current password checkers typically use counters of occurrence (e.g., one upper case character, two numerals, at least seven characters, etc.). These types of strength checkers may allow "weak" passwords to be accepted by a site or system. For example, a user, named John Smith, may select "jOHNsMITH12" as a password. This may pass a conventional checker by having at least one upper case character, at last one lower case character, at least two numerals, and at least seven characters. However, it may not be hard for someone to guess this password.

In different embodiments of the present invention, computing device checks a proposed password by decomposing the password into more basic words and/or numbers and analyzing how the password uses the smaller blocks to create the password by applying a set of rules and scoring the password. If the score is above a predetermined threshold, the user may be notified that the proposed password is accepted. However, if the score is below the threshold, the user may be notified that the password is unacceptable and to submit another proposed password. The user may also be notified as to one or more reasons the password was not accepted.

In one embodiment, the site utilizes three rules to determine whether to accept a proposed password: 1) concatenation, 2) insertion, and 3) replacement. Note that different rules and different numbers of rules can be used in other embodiments. Concatenation is when one word is appended to the beginning or end of another word. Words, as used herein, can be mean actual words, names, acronyms, numbers, and/or characters. An example of a concatenation is "blueink" which is the word "blue" appended to the beginning of the word "ink" or equivalently, the word "ink" appended to the end of the word "blue."

Insertion is when a word is inserted into or within another word. One example is "binklue" in which "ink" is inserted after the letter "b" in "blue." Another example is "bi435g" in which the word "435" is inserted after the letter "i" in "big." In another example, "F@ish@ing" is "Fishing" but with the character "@" inserted after both "F" and "h."

Replacement is when one or more letters in the password are replaced. For example, in "Trul4", the "y" in "Truly" was replaced with "4." In another example, "jOHNsMITH13" is a password in which the "2" in "jOHNsMITH12" is replaced with "3." As will be appreciated by those in the art, there are many different ways to break down a word in addition to the rules described above.

Figure 1:
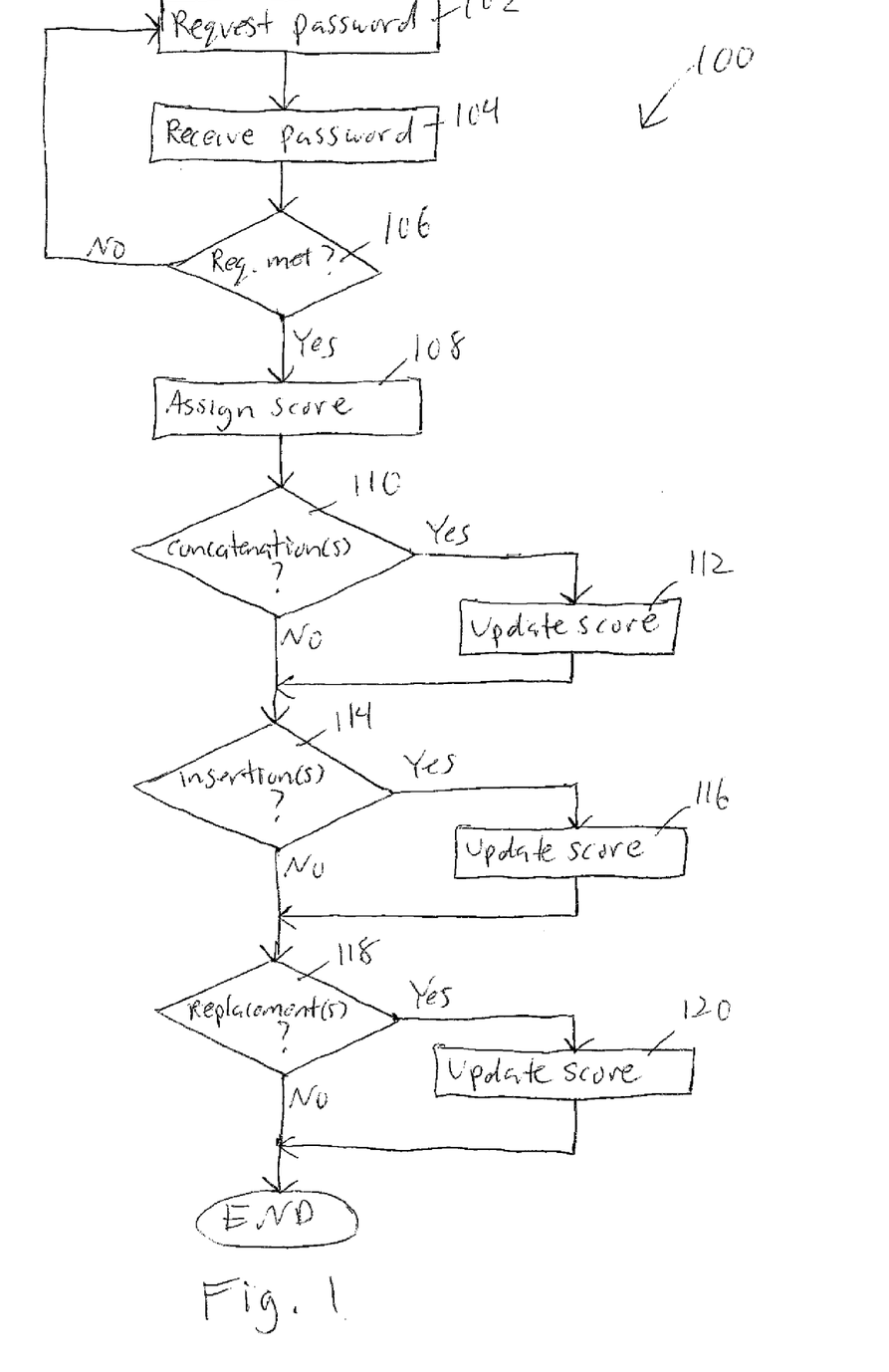
FIG. 1 is an exemplary flow chart showing steps a service provider performs to determine a score for a proposed password, according to one embodiment.

FIG. 1 is an exemplary flow chart 100 showing steps a service provider performs to determine a score for a proposed password, according to one embodiment. At step 102, a service provider requests a password from a user at step 102. The request may be triggered by different actions, such as the user creating an account with the service provider. The request may be communicated electronically to a user computing device, such as a smart phone, PC, computing tablet, etc. from a server or processor of the service provider.

In response, the user communicates a password from the user device, which is received by the service provider at step 104. The user may enter the password using a keypad, microphone, or other data input/entry means on the user device. The password may be a combination of letters, numbers, and symbols (generally referred to as characters). In this example, the proposed password is "Flat3dog", which the user may enter through a keypad. Once the user-proposed password is received, a determination is made, at step 106, whether password requirements are met. The service provider may require the password to be a minimum length, contain one or more specific characters types, and/or contain a minimum number of one or more specific character types. In this example, the password is required to be at least seven characters long and contain at least one capital letter and at least one number, which is met by "Flat3dog".

If the password requirements are not met by the proposed password, the user may be requested to submit another password, at step 102. Once an acceptable password has been received, the password may be assigned an initial score at step 108. In a typical process, once the password is deemed acceptable by the service provider, the proposed password is accepted with no further analysis.

However, with embodiments of the present invention, the proposed password is further processed as follows. The initial score may be based on specific rules for the service provider. For example, the score may be a function of password length, the number of different characters used, and the number of characters used that are not lower case (or upper case) letters, with the longer the length, the larger number of different characters used, and/or the higher number of non letter characters used, the higher the score. Continuing with the example, "Flat3dog" may be assigned an initial score of 54.

Next, the proposed password is analyzed for concatenations at step 110 by first identifying all words within the password. This may include all possible words, numbers, and characters or a subset or a combination, such as only whole words or names. For example, "Flat3dog" may be decomposed into the words "Flat", "at", "3", "do", and "dog". Based on this, there may be two concatenations: "3" appended to the end of "Flat" (or vice versa) and "3" appended to the front of "dog" (or vice versa). Thus, as determined at step 110, the proposed password has concatenations, which causes the password score to be updated at step 112. For example, if the initial score was 54, the updated score may now be 60 (e.g., applying a rule allocating two points for each concatenation). Note that in one embodiment, no initial score may be assigned, and the first score would be based on the result of the first rule or test, which in this embodiment would be concatenations.

Next, the password is analyzed to determine, at step 114, whether there are any insertions. In the "Flat3dog" example, there is one insertion of a "3" into "Flatdog." If there is one or more insertions, the score is updated at step 116. Continuing with the example, the score may not be updated to a 65 (e.g., applying the rule of five points to each insertion).

Next, the password is analyzed to determine, at step 118, whether the password has any replacements. If one or more replacements are found, the score is again updated, at step 120. However, as with the current example, there are no replacements, the score is not updated. Once a rule set is finished, the password score is finalized. In this case, the score for "Flat3dog" is 65. Note that the rules described above are not limiting. The rules can be applied in different order, additional rules may be added, one or more of the above rules may be deleted, etc. One or more steps described herein may also be performed in different order, combined, or omitted.

In another example, the proposed password is "FlaDogt". First, all words are identified: "Flat" and "Dog". The insertion rule is triggered, but not the concatenation rule or the replacement rule. Thus, a score is given to "FlaDogt" based only on the insertion rule. In another example, "ft" is analyzed. There are no concatenations or insertions, but there is a replacement, i.e., "" may have replaced "ee", "ea", "la", etc. Here, the score is based on the replacement rule(s).

What rules to apply and how to score may depend on the password checker and can vary. For example, concatenation may have a lower weight than insertion because it is easier to determine a concatenated password than one with an insertion. Even with a rule, there may be different weights. For example, with insertions, an insertion before the last letter may have a lower weight than an insertion in the middle of the word, again due to ease of determination. A number insertion may have a lower weight than a word insertion. In one embodiment, the lower the score, the less secure or strong the password is.

Passwords can be decomposed using a lexicographic scanner, where the language expressed is a regular language, and the scanner is similar to a parser of a computer program compiler. Customized programs may be written to decompose passwords as well.

Figure 2A:
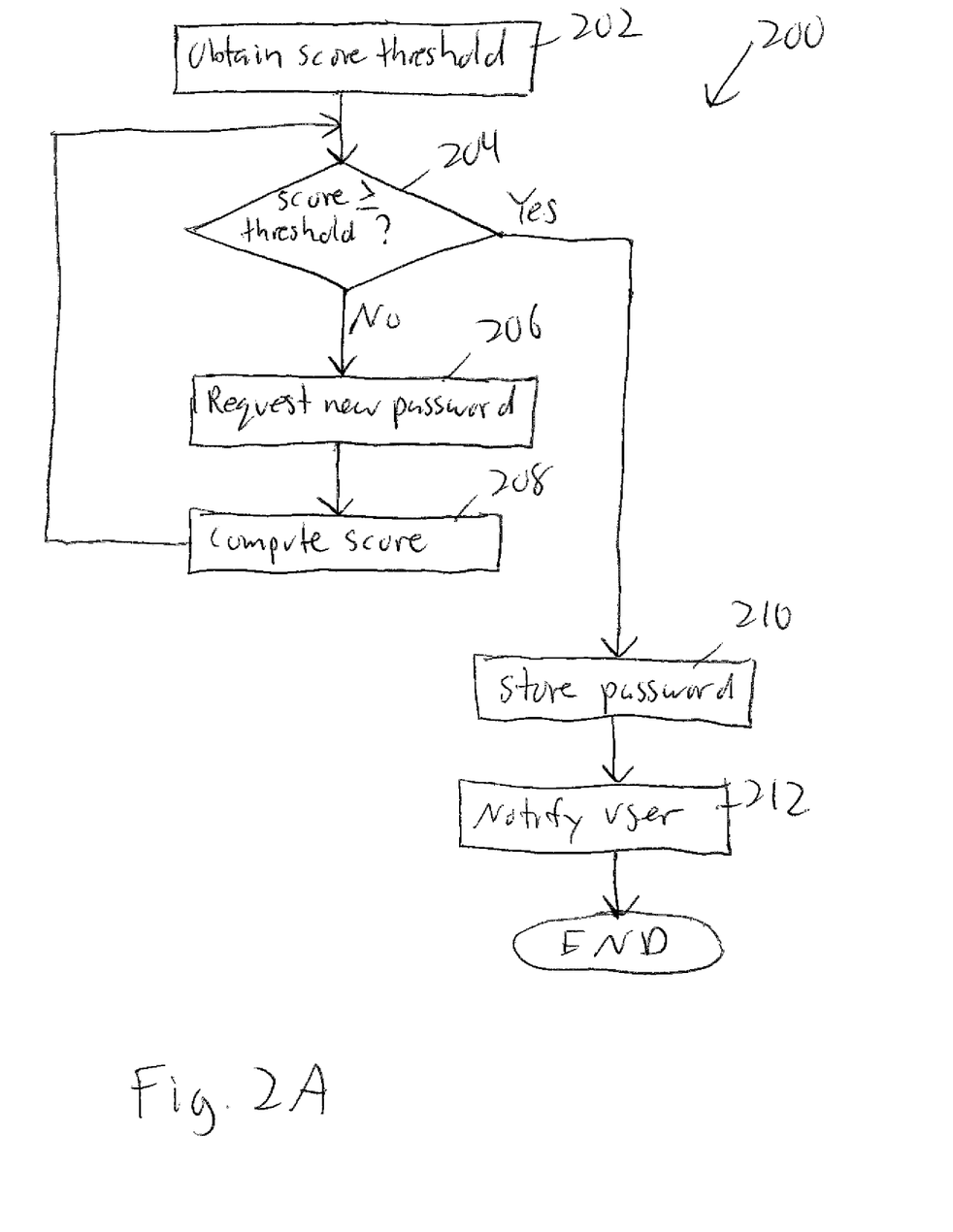
FIG. 2A is a flowchart showing a process to check the strength of a password according to one embodiment.

FIG. 2A is a flowchart 200 showing a process to check the strength of a password according to one embodiment. Flowchart 200 begins at step 202 with the service provider determining a score threshold to compare with the score for the user-proposed password determined above, such as in FIG. 1 and corresponding text. The score threshold may vary depending on the type of access, data, use, or system. For example, for a password to be used to access very sensitive information, such as identity information, or to allow the user access to money, such as access to a bank account, the threshold may be a higher number than a password used to access content on a site, such as viewing articles where the user has to register first to view. Continuing with the earlier example, a score threshold of 60 may be used.

Next, at step 204, a determination is made whether the computed score is greater than or equal to the score threshold. If not, the proposed password may be deemed to not be strong enough for the user and/or the service provider. In that case, the service provider may request the user to submit a new password at step 206, which can be similar to step 102 in FIG. 1. However, the request at step 206 may also include one or more reasons why the proposed password was not acceptable. For example, the user may be informed that there is not enough separation or differentiation between the combination of words in the password. By providing the user such information, the user may be better equipped to submit a password that is more likely to be accepted.

After requesting a new password, the service provider receives the new password and computes a score for the new password at step 208, such as with steps illustrated in FIG. 1 and corresponding text. Once the score for the new password is determined, it is compared with the score threshold again at step 204. The service provider may allow the user to continually submit passwords until one meets or exceeds the score threshold, or the service provider may only allow the user a limited amount of submissions before it either assigns the user a password or some other action.

Upon receiving a password that meets or exceeds the service provider's score threshold, the password is stored at step 210, such as in a database, memory, cloud, or other storage means controlled or managed by the service provider. The password may be stored and associated with the newly created user account, along with any account identifiers, such as a user name, email address, phone number, account number, etc.

The service provider may then notify the user, at step 212, that the submitted password has been accepted. The notification may be electronically to the user device, such as in a text message, email, or voice message. The user may then be granted access to the user account with the service provider.

Figure 2B:
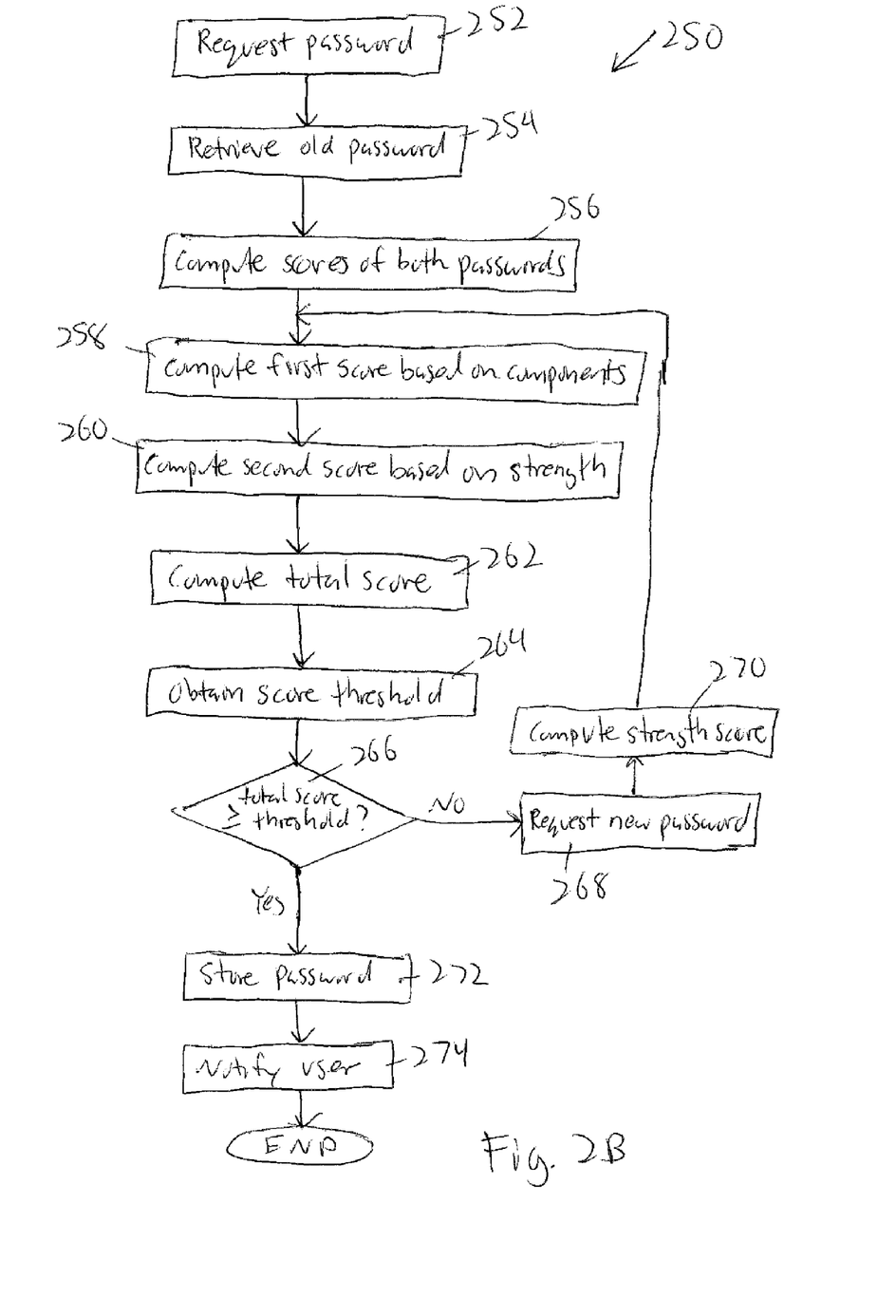
FIG. 2B is a flowchart showing a process to check or compare the strength of a password to a previous password according to one embodiment.

FIG. 2B is a flowchart 250 showing a process to check or compare the strength of a password to a previous password according to one embodiment. At step 252, the service provider requests a new password from a user. The request may be sent, as in step 102 of FIG. 1, electronically to a user device, such as a PC, computing tablet, or smart phone. However, one difference is that the user already has an account with the service provider and has already accessed or logged onto the account, such as by entering authenticating information like a user name, email address, phone number, and a password or PIN. The request may be made because the service provider requires the password to change every predetermined time period for security reasons, the password may have been compromised, or some other reason. The service provider receives the password and determines whether any minimum requirements are met, such as described in FIG. 1 at steps 104 and 106.

Once the new proposed password has met any service provider requirements, the service provider typically accepts the new password for the user account or access. This may result in an easily determinable password by fraudsters, such as when the new password is logically very similar to the old password and/or is an easy password to guess regardless of the old password.

In embodiments of the present invention, the new password is not automatically accepted, but rather goes through further analysis as follows. First, the service provider retrieves the old or current password at step 254, such as from the user's stored account information. Thus, the service provider has both a newly proposed password from the user and the current password the user enters for authentication with the service provider.

The two passwords (the new proposed password and the old/current password) are decomposed and scored at step 256, such as described in FIG. 1. If the two passwords are similar, their scores may also be similar. The scores are based solely on each password itself and not on any comparisons with other passwords. For example, if the old password was "johnsmith123" and the new proposed password is "johnsmith124", the old password may be assigned a score of 40 and the new password may be assigned a score of 42. Both passwords use only concatenation and not insertions or replacements. The new password may have a slightly higher score due to the non-sequential nature of "124" as opposed to "123". In one embodiment, only the new proposed password is assigned an individual strength score.

Next, at step 258, a first similarity score based on components or words of the two passwords is computed. Passwords that are very close to one another may be result in a low similarity score (or a high similarity score if high scores denote similar passwords). This may be the case even if both passwords are very unique, such as "Xci4%0@_iC#*". With the previous example, the similar score for "johnsmith123" and "johnsmith124" would have a similarity score indicating very similar passwords (e.g., ones that differ only by a number at the end), such as a 1 or a 97 (on a 100 point scale). To the contrary, a proposed password of "gregjones456" would have a similar score indicating very different passwords, even though the format or structure is the same. The proposed password is composed of words that are not included anywhere in the old password.

The service provider also determines, at step 260, a second similarity score based on rules (e.g., concatenation, insertion, replacement) for the two passwords. For example, using the above example, both passwords ("jimmysmith123" and "jimmysmith124") use concatenation multiple times, but no other rules. Thus, this will generate a score indicating very similar, if not the same, rule similarities, such as a 0/1 or 97-100 (on a 100 point scale).

To the contrary, a proposed password of "88ji42mmy#smitYEt123" would have a score indicating very different rules, even though it can be decomposed into words or components of the original password. The original password only uses concatenation, while the proposed password uses concatenation, insertion, and replacement multiple times. Note that the process can apply to all or more than one previous user passwords, not just the current password.

A "final" or total score for the proposed password can be determined, at step 264. The total score may be a function of the individual strength score (determined at step 256), the first similarity score based on words (determined at step 258), and the second similarity score based on rules (determined at step 260). In other embodiments, additional factors can be included and one or more of the scores can be omitted. Continuing with the above example, the proposed new password "jimmysmith124" may receive a final score of 44 because it is similar to the original password both in similarity of words and similarity of rules.

A threshold score may be obtained, at step 264, or earlier. Factors for determining a threshold score may be the same as described previously at step 202 of FIG. 2A or may be the same as the threshold score previously used by the service provider.

The final score is then compared with the threshold score and a determination is made, at step 266, whether the final score is greater than or equal to the threshold score. If not, that indicates the new proposed password would not be acceptable to the service provider as being weak and/or too similar to the old or current password. In that case, the service provider may request the user to submit a new password, at step 268, and then compute the strength of the new password at step 270. These steps may be the same or similar to steps described in other embodiments. The analysis may then continue at step 258 to eventually determine whether the newly proposed password meets or exceeds the set score threshold.

If so, as determined at step 266, the new password is stored, at step 272, and the user notified, at step 274. Storing and notification may be the same or similar as steps 210 and 212 in FIG. 2A.

As a result, the service provider is able to better analyze the strength of a proposed password for a new account or for a preexisting account. A stronger password provides the user with additional security so that fraudsters are less likely to guess the user's password and provides benefits to the service provider, such as less unauthorized access to the service provider site and a stronger reputation of a secure site.

Note that the above description focuses on a user submitted a proposed password to be checked by the service provider. However, in other embodiments, the checked password does not need to be a proposed password. Rather, the checked password may be one submitted by the user as part of a login or authentication process, i.e., the checked password is the currently used user password. Thus, using techniques described herein, a service provider may check a user's current password for strength.

Furthermore, in other embodiments, when a password (existing or proposed) is determined to be weak, i.e., having a score less than a predetermined score threshold, that password may be flagged or otherwise noted in the system. The service provider can use this information to take action, such as notifying the user of a weak password and requesting a new password to be submitted, or inform the user that the password had already been previously submitted and was unacceptable.

Figure 3:
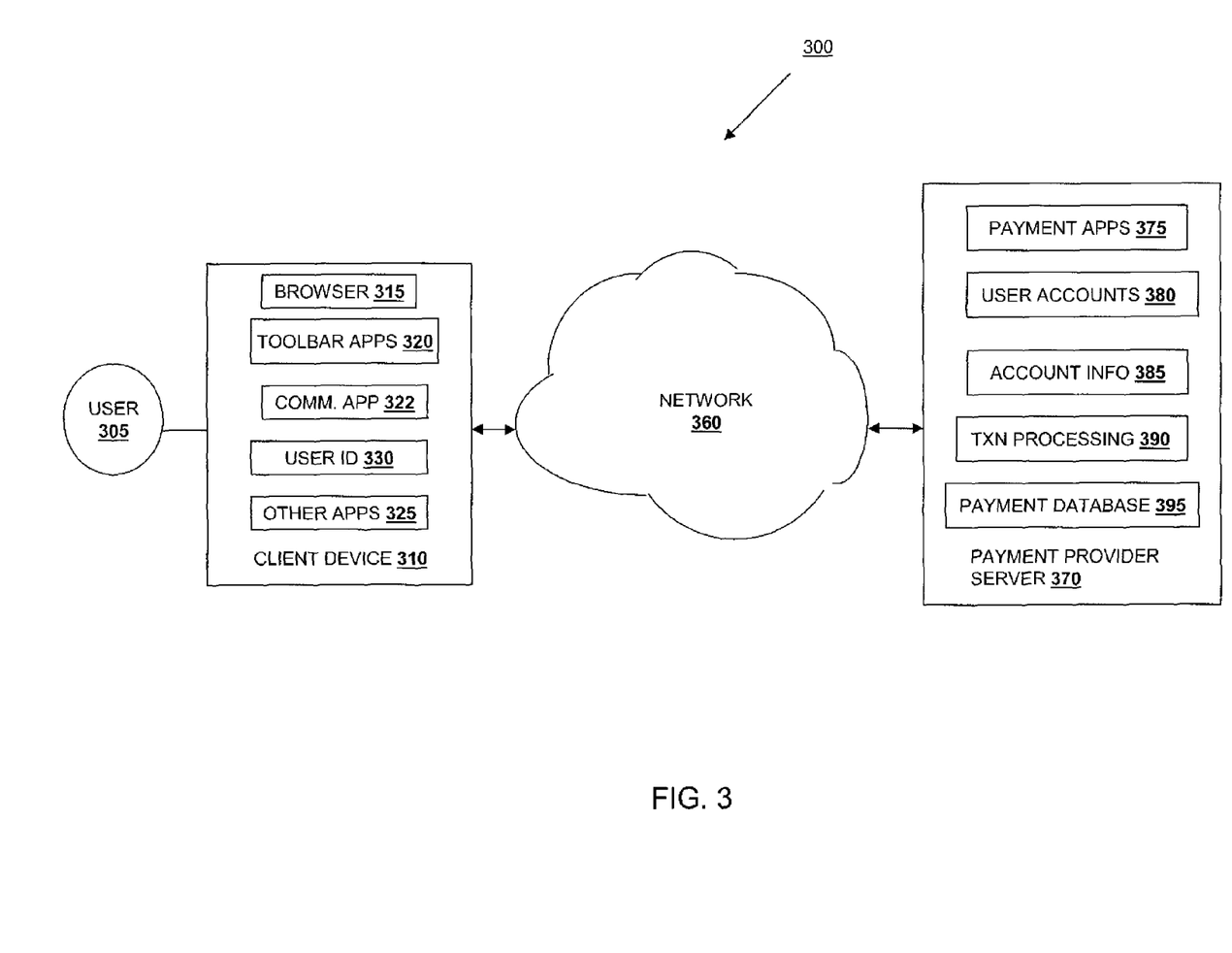
FIG. 3 is block diagram of a networked system suitable for implementing the process of FIGS. 1 and 2 according to an embodiment.

FIG. 3 is a block diagram of a networked system 300 configured to handle a communication or transaction between a user and a service provider, such as a payment provider, as described above, in accordance with an embodiment of the invention. System 300 includes a user device 310 and a payment provider server 370 in communication over a network 360. Payment provider server 370 may be maintained by a payment provider, such as PayPal, Inc. of San Jose, Calif. A user 305, such as a consumer desiring to access a site or account through the payment provider, utilizes user device 310 communicate with payment provider server 370.

User device 310 and payment provider server 370 may each include one or more processors, memories, and other appropriate components for executing instructions such as program code and/or data stored on one or more computer readable mediums to implement the various applications, data, and steps described herein. For example, such instructions may be stored in one or more computer readable media such as memories or data storage devices internal and/or external to various components of system 300, and/or accessible over network 360.

Network 360 may be implemented as a single network or a combination of multiple networks. For example, in various embodiments, network 360 may include the Internet or one or more intranets, landline networks, wireless networks, and/or other appropriate types of networks.

User device 310 may be implemented using any appropriate hardware and software configured for wired and/or wireless communication over network 360. For example, in one embodiment, the user device may be implemented as a personal computer (PC), a smart phone, personal digital assistant (PDA), laptop computer, and/or other types of computing devices capable of transmitting and/or receiving data, such as an iPad™ from Apple™.

User device 310 may include one or more browser applications 315 which may be used, for example, to provide a convenient interface to permit user 305 to browse information available over network 360. For example, in one embodiment, browser application 315 may be implemented as a web browser or mobile Internet app configured to view information available over the Internet. User device 310 may also include one or more toolbar applications 320 which may be used, for example, to provide client-side processing for performing desired tasks in response to operations selected by user 305. In one embodiment, toolbar application 320 may display a user interface in connection with browser application 315.

User device 310 may further include other applications 325 as may be desired in particular embodiments to provide desired features to user device 310. For example, other applications 325 may include security applications for implementing client-side security features, programmatic client applications for interfacing with appropriate application programming interfaces (APIs) over network 360, or other types of applications. Applications 325 may also include email, texting, voice and IM applications that allow user 305 to send and receive emails, calls, and texts through network 360, as well as applications that enable the user to communicate passwords and other information with the payment provider as discussed above. User device 310 includes one or more user identifiers 330 which may be implemented, for example, as operating system registry entries, cookies associated with browser application 315, identifiers associated with hardware of user device 310, or other appropriate identifiers, such as used for payment/user/device authentication. In one embodiment, user identifier 330 may be used by a payment service provider to associate user 305 with a particular account maintained by the payment provider as further described herein. A communications application 322, with associated interfaces, enables user device 310 to communicate within system 300.

Payment provider server 370 may be maintained, for example, by an online payment service provider which may provide payment services for user 305. In this regard, payment provider server 370 includes one or more payment applications 375 which may be configured to interact with user device 310 over network 360 to facilitate the purchase of goods or services by user 305 of user device 310 by various means, such as online, offline, mobile, etc.

Payment provider server 370 also maintains a plurality of user accounts 380, each of which may include account information 385 associated with individual users. For example, account information 385 may include private financial information of users of devices such as account numbers, passwords, device identifiers, user names, phone numbers, credit card information, bank information, or other financial information which may be used to facilitate online transactions by user 305. Advantageously, payment application 375 may be configured to interact with user 305 during a transaction to track and manage purchases made by users and allow the user to access and manage the user's account.

A transaction processing application 390, which may be part of payment application 375 or separate, may be configured to receive information from a user device and/or a merchant device (not shown) for processing and storage in a payment database 395. Transaction processing application 390 may include one or more applications to process information from user 305 for processing a payment. Payment application 375 may be further configured to determine the existence of and to manage accounts for user 305, as well as create new accounts if necessary, including determining a password for a new or existing account.

Figure 4:
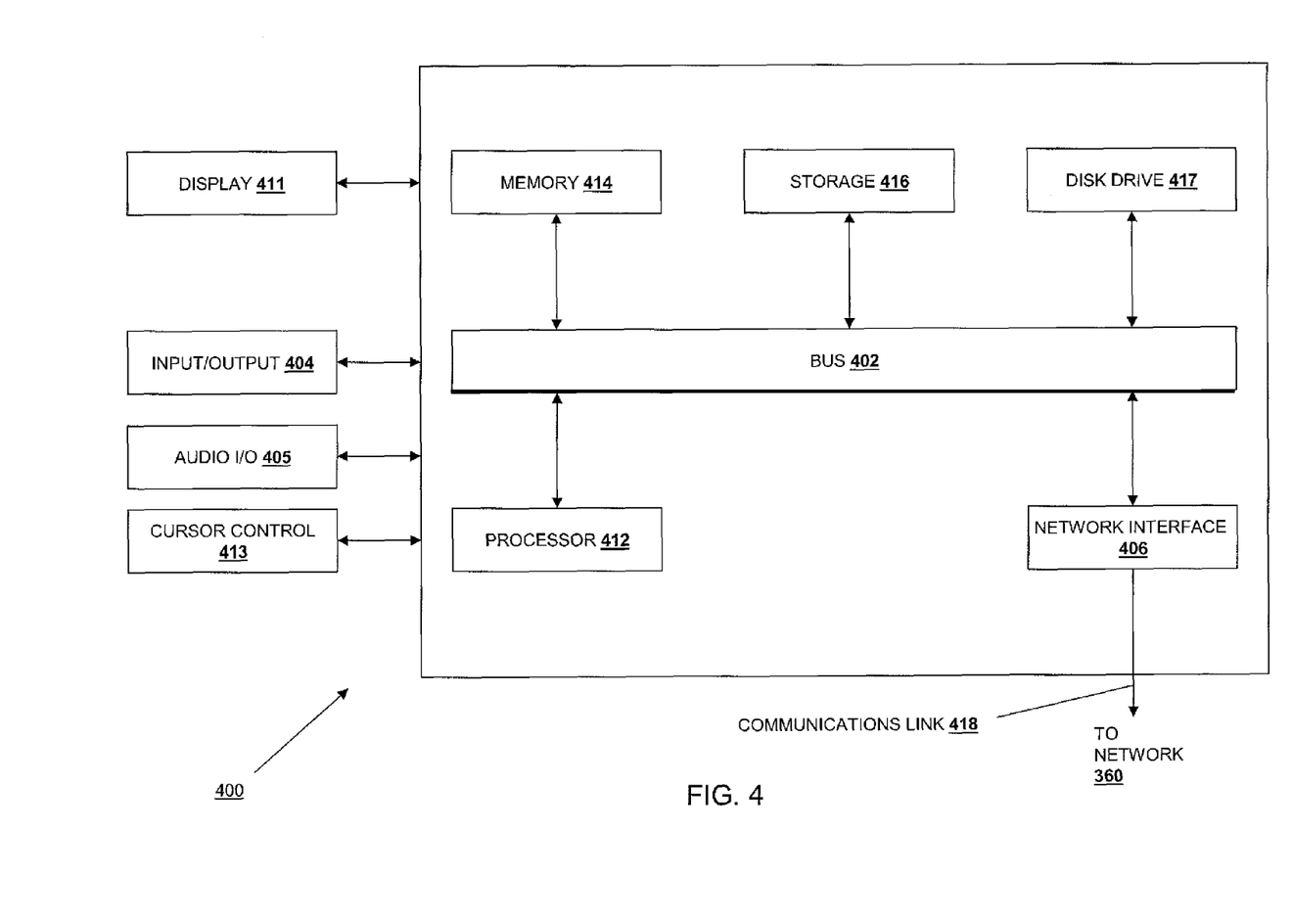
FIG. 4 is a block diagram of a computer system suitable for implementing one or more components in FIG. 3 according to one embodiment of the present disclosure.

FIG. 4 is a block diagram of a computer system 400 suitable for implementing one or more embodiments of the present disclosure. In various implementations, computer system 400 may be used to check a password strength, communicate with a user, communicate with a password checker, or communicate with a system or site requiring password entry. The system or device may comprise a personal computing device (e.g., a personal computer, laptop, smart phone, PDA, Bluetooth device, key FOB, badge, etc.) capable of communicating with a network.

Computer system or device 400 includes a bus 402 or other communication mechanism for communicating information data, signals, and information between various components of computer system 400. Components include an input/output (I/O) component 404 that processes a user action, such as selecting keys from a keypad/keyboard, selecting one or more buttons or links, etc., and sends a corresponding signal to bus 402. I/O component 404 may also include an output component, such as a display 411 and a cursor control 413 (such as a keyboard, keypad, mouse, etc.) for a user to enter a password. An optional audio input/output component 405 may also be included to allow a user to use voice for inputting information by converting audio signals, such as a spoken password. Audio I/O component 405 may allow the user to hear audio. A transceiver or network interface 406 transmits and receives signals between computer system 400 and other devices, such as another user device, a merchant server, or a service provider server via a network. In one embodiment, the transmission is wireless, although other transmission mediums and methods may also be suitable, A processor 412, which can be a micro-controller, digital signal processor (DSP), or other processing component, processes these various signals, such as for display on computer system 400 or transmission to other devices via a communication link 418. Processor 412 may also control transmission of information, such as cookies or IP addresses, to other devices.

Components of computer system 400 also include a system memory component 414 (e.g., RAM), a static storage component 416 (e.g., ROM), and/or a disk drive 417. Computer system 400 performs specific operations by processor 412 and other components by executing one or more sequences of instructions contained in system memory component 414, Logic may be encoded in a non-transitory computer readable medium, which may refer to any medium that participates in providing instructions to processor 412 for execution. Such a medium may take many forms, including but not limited to, non-volatile media, volatile media, and transmission media. In various implementations, non-volatile media includes optical or magnetic disks, volatile media includes dynamic memory, such as system memory component 414, and transmission media includes coaxial cables, copper wire, and fiber optics, including wires that comprise bus 402. In one embodiment, the logic is encoded in non-transitory computer readable medium. In one example, transmission media may take the form of acoustic or light waves, such as those generated during radio wave, optical, and infrared data communications.

Some common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, or any other medium from which a computer is adapted to read.

In various embodiments of the present disclosure, execution of instruction sequences to practice the present disclosure may be performed by computer system 400. In various other embodiments of the present disclosure, a plurality of computer systems 400 coupled by communication link 418 to the network (e.g., such as a LAN, WLAN, PTSN, and/or various other wired or wireless networks, including telecommunications, mobile, and cellular phone networks) may perform instruction sequences to practice the present disclosure in coordination with one another.

Where applicable, various embodiments provided by the present disclosure may be implemented using hardware, software, or combinations of hardware and software. Also, where applicable, the various hardware components and/or software components set forth herein may be combined into composite components comprising software, hardware, and/ or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, persons of ordinary skill in the art will recognize that changes may be made in form and detail without departing from the scope of the present disclosure. Thus, the present disclosure is limited only by the claims.

What is claimed is:

1. A system, comprising:
a non-transitory memory; and
one or more hardware processors coupled to the non-transitory memory and configured to read instructions from the non-transitory memory to cause the system to perform operations comprising:
receiving, by a service provider, a password from a user;
decomposing the password into components contained in the password;
determining whether the password is formed by the components using one or more rules of concatenation, insertion, and replacement;
determining a score for the password based on the one or more rules used for forming the password with at least one rule having a different weighting than another rule; and
comparing the score to a threshold score.

2. The system of claim 1, wherein the operations further comprise accepting the password if the score is greater than or equal to the threshold score.

3. The system of claim 1, wherein the components comprise known words, names, numbers, and characters.

4. The system of claim 1, wherein the password is formed using all the rules.

5. The system of claim 1, wherein none of the rules have the same weight.

6. The system of claim 1, wherein the password is a proposed password by the user.

7. The system of claim 1, wherein an initial score is assigned to the password based on types of individual characters used for forming the password and wherein the score is determined by updating the initial score based on whether the password is formed by the components using the one or more of the rules of concatenation, insertion, and replacement.

8. The system of claim 1, wherein the operations further comprise comparing similarities between the password and a second password for the user, determining a similarity score between the password and the second password based on the comparing; and comparing the similarity score to a threshold.

9. The system of claim 1, wherein the password is flagged by the service provider if the score is below the threshold score.

10. A system, comprising:
a non-transitory memory; and
one or more hardware processors coupled to the non-transitory memory and configured to read instructions from the non-transitory memory to cause the system to perform operations comprising:
receiving a first password from a user;
retrieving a second password for the user;
decomposing the first and the second passwords into components contained in the passwords;
determining whether the passwords are formed by the components using one or more rules of concatenation, insertion, and replacement;
comparing similarities between the first password and the second password comprising identifying rules and components of the first and second passwords, comparing similarities of the rules and the components, and determining a first similarity score for the rules and a second similarity score for the components;
determining a score between the first password and the second password based on the comparing; and
comparing the score to a threshold score.

11. The system of claim 10, wherein the operations further comprise accepting the first password if the score is greater than or equal to the threshold score.

12. The system of claim 10, wherein the score is based on a function of the first and second similarity scores.

13. The system of claim 10, wherein the operations further comprise retrieving a previously used third password by the user, comparing similarities between the first password and the second and third passwords, and determining a score between the first password and the second and third passwords.

14. The system of claim 12, wherein the operations further comprise determining a strength score for the first password and the score is further based on a function of the strength score.

15. The system of claim 10, wherein the first password is flagged by the service provider if the score is below the threshold score.

16. A non-transitory machine-readable medium having stored thereon machine-readable instructions executable to cause a machine to perform operations comprising:
receiving, by a service provider, a password from a user;
decomposing the password into components contained in the password;
determining whether the password is formed by the components using one or more rules of concatenation, insertion, and replacement;
determining a score for the password based on the one or more rules with at least one rule having a different weighting than another rule; and
comparing the score to a threshold score.

17. The non-transitory machine-readable medium of claim 16, wherein the operations further comprise accepting the password if the score is greater than or equal to the threshold score.

18. The non-transitory machine-readable medium of claim 16, wherein the password is formed using all the rules.

19. The non-transitory machine-readable medium of claim 16, wherein an initial score is assigned to the password based on types of individual characters used for forming the password and wherein the score is determined by updating the initial score based on whether the password is formed by the components using the one or more of the rules of concatenation, insertion, and replacement.

20. The non-transitory machine-readable medium of claim 16, wherein the password is a proposed password by the user.

21. The non-transitory machine-readable medium of claim 16, wherein the operations further comprise comparing similarities between the password and a second password for the user, determining a similarity score between the password and the second password based on the comparing; and comparing the similarity score to a threshold.

22. The non-transitory machine-readable medium of claim 16, wherein the password is flagged by the service provider if the score is below the threshold score.

23. A non-transitory machine-readable medium having store thereon machine-readable instructions executable to cause a machine to perform operations comprising:

receiving a first password from a user;

retrieving a second password for the user;

decomposing the first and the second passwords into components contained in the passwords;

determining whether the passwords are formed by the components using one or more rules of concatenation, insertion, and replacement;

comparing similarities between the first password and the second password comprising identifying rules and components of the first and second passwords, comparing similarities of the rules and the components, and determining a first similarity score for the rules and a second similarity score for the components;

determining a score between the first password and the second password based on the comparing; and comparing the score to a threshold score.

24. The non-transitory machine-readable medium of claim 23, wherein the operations further comprise accepting the first password if the score is greater than or equal to the threshold score.

25. The non-transitory machine-readable medium of claim 23, wherein the score is based on a function of the first and second similarity scores.

26. The non-transitory machine-readable medium of claim 23, wherein the operations further comprise retrieving a previously used third password by the user, comparing similarities between the first password and the second and third passwords, and determining a score between the first password and the second and third passwords.

27. The non-transitory machine-readable medium of claim 25, wherein operations further comprise determining a strength score for the first password and the score is further based on a function of the strength score.

\* \* \* \* \*